United States Patent [19]
Lawton et al.

[11] 3,970,635
[45] July 20, 1976

[54] FIRE RETARDANT POLYESTER FIBERS

[75] Inventors: Ernest L. Lawton, Durham; Eugene L. Ringwald, Raleigh, both of N.C.

[73] Assignee: Monsanto Company, St. Louis, Mo.

[22] Filed: Jan. 28, 1974

[21] Appl. No.: 437,412

[52] U.S. Cl............ 260/45.8 R; 260/40 P; 260/927 R; 260/937; 260/DIG. 24
[51] Int. Cl.² ............ C08K 5/52; C08L 67/02
[58] Field of Search ......... 260/45.8 R, 927 R, 937, 260/40 P, DIG. 24

[56] References Cited
UNITED STATES PATENTS

| | | | |
|---|---|---|---|
| 2,520,090 | 8/1950 | Barrett | 260/930 |
| 2,952,701 | 9/1960 | McConnell et al. | 260/45.8 R |
| 2,952,701 | 9/1960 | McConnell et al. | 260/927 |
| 2,960,528 | 11/1960 | McConnell et al. | 260/937 |
| 2,974,158 | 3/1961 | Lanham | 260/927 |
| 3,283,037 | 11/1966 | Davis | 260/45.8 R |
| 3,488,407 | 1/1970 | Schall et al. | 260/45.8 R |
| 3,511,857 | 5/1970 | Baranauckas et al. | 260/45.8 R |
| 3,576,780 | 4/1971 | Jackson, Jr. | 260/30.6 |
| 3,658,634 | 4/1972 | Yanagi et al. | 161/175 |
| 3,725,510 | 4/1973 | Dever et al. | 260/45.8 R |
| 3,789,091 | 1/1974 | Anderson et al. | 260/927 |

OTHER PUBLICATIONS

Hilado, "Flammability Handbook for Plastics", 1969, pp. 85, 86.

Primary Examiner—Ronald W. Griffin
Attorney, Agent, or Firm—Robert L. Broad, Jr.

[57] ABSTRACT

Fire retardant qualities are incorporated into polyester fibers by adding to the polymer, prior to spinning thereof into filaments, not more than about 20 percent, based on the weight of the polymer, of a compound containing two six membered phosphorus-containing heterocyclic rings having carbon, oxygen and phosphorus in the heterocyclic ring.

12 Claims, 1 Drawing Figure

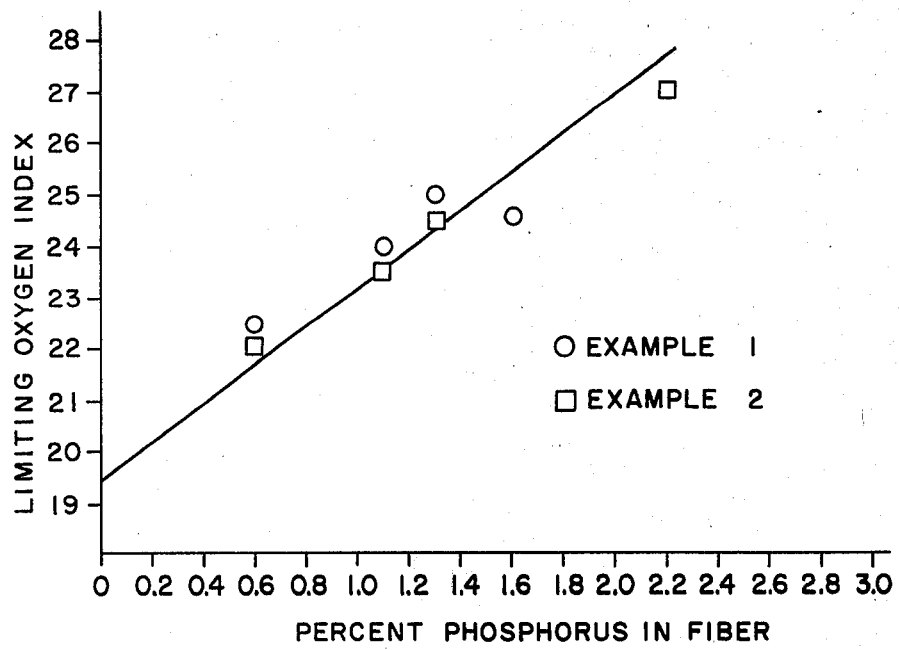

FIRE RETARDANT POLYESTER FIBERS

This invention relates to polyesters produced by condensation reactions of polymethylene glycols and dicarboxylic acids or reactive derivates thereof.

It is well known that the polymeric polyesters prepared by the condensation of a glycol or its functional derivatives and a dicarboxylic acid or a polyester-forming derivative thereof, such as an acid halide, a salt, or a simple ester of a dibasic acid and a volatile monohydric alcohol are excellent fiber-forming polymers. Commercially, highly polymeric polyesters are prepared, for example, by the condensation of terephthalic acid or dimethyl terephthalate and a polymethylene glycol containing from about 2 to 10 carbon atoms, and particularly ethylene glycol, generally as taught in U.S. Pat. No. 2,465,319 and improvements thereof. These polyesters are relatively insoluble, chemically inactive, hydrophobic materials capable of being formed into filaments which can be cold-drawn to produce textile fibers of superior strength and pliability. It has long been considered desirable to impart flame retardant qualities in these polyester fibers so that fabrics, particularly those containing natural fibers such as cotton, might thereby be rendered nonburnable. A wide variety of techniques have been employed to produce flame retardancy in polyesters, including the co-polymerization and transesterification of monomers which contain halogen and phosphorus, and the incorporation of these elements into the polymer by means of additives or carriers.

By adding a phosphorus or halogen-containing compound while the polymer is in melt phase, the compound, or the fire resisting elements thereof will more likely remain in the fiber, even when exposed to subsequent washing or dry cleaning operations.

Phosphorus, bromine and chlorine have long been known as fire retardant elements, particularly adaptable for use in polymeric materials. These elements have been introduced into the polymers through a number of compounds; the problem of introduction being one of compatability with the polymeric materials and reaction. Incompatibility, in the sense intended herein, of course, results in degradation or alteration of the polymer and of the fibers formed from the polymer. Bromine, chlorine and phosphorus, as elements cannot be added to polyethylene terephthalate prior to spinning without causing serious degradation.

The addition of low molecular weight compounds to polyesters in melt form is disadvantageous usually because the volatility of the compound will cause it to be removed by distillation; it may act as a plasticizer or thinner for the polymer to such an extent that the polymer cannot be spun into fibers, and it may cause the melting point of the polymer to be lowered to such an extent that it will have limited use when spun into fibers and it may react with the ester linkages in the polymer chain resulting in molecular weight loss. It may also be easily removed when the fiber is chemically swelled and opened while being subjected to conventional carrier-assisted dyeing. Some of these disadvantages may be overcome if the elements of phosphorus or halogen are part of a larger molecule such as polymeric material. The polymeric additive need not be compatible with the polyester in the sense that it could or would become a part of the polyester chain; but physical compatibility is essential.

It is an object of this invention to provide a compound suitable for use as a fire retardant additive in polyethylene terephthalate.

It is another object of this invention to provide a method of preparing fire retardant polyethylene terephthalate fibers.

Briefly the objects of this invention are accomplished by adding, prior to the spinning of the polyethylene terephthalate polymer into filaments, not more than about 20 percent, based on the weight of the polymer, of a compound having the general formula:

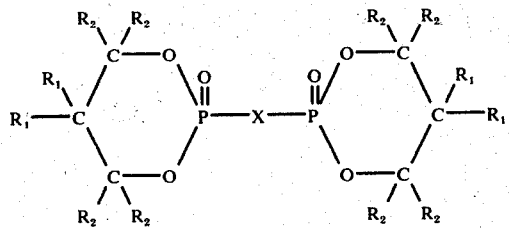

Wherein $R_1$ is an alkyl group containing 1–5 carbon atoms; $R_2$ is a radical selected from the group consisting of H and an alkyl group containing 1–5 carbon atoms; and X is a divalent radical selected from the group consisting of

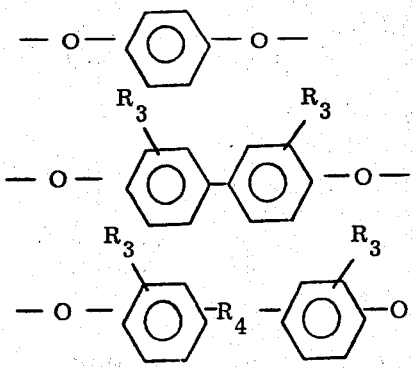

Where $R_3$ is a radical selected from the group consisting of hydrogen or a 1–5 carbon alkyl group, and $R_4$ is a radical selected from the group consisting of an alkyl radical having 1–10 carbon atoms, and $SO_2$.

To further understand the invention, reference will be made to the attached drawing that forms a part of this application in which:

The FIGURE is a graph showing how the limiting oxygen index in polyester fibers is affected by phosphorus content as included by the additives of Examples 1 and 2.

By polyester fibers, as used herein, is meant a manufactured fiber in which the fiber-forming substance is any long chain synthetic polymer composed of at least 85% by weight of an ester of a dihydric alcohol and terephthalic acid.

We have discovered that these compounds do not cause serious degradation of the polyester polymer (or otherwise interfere with subsequent fiber formation). We have also discovered that, unlike structurally similar compounds, these compounds remain fast in the fiber when subjected to conventional carrier assisted dyeing. Detailed descriptions of some of these compounds and their preparations are found in U.S. Pat. No. 2,974,158.

The additive may be added at any convenient stage prior to spinning. Up to about 20% based on the final weight of the modified polymer can be tolerated. A minimum effective level is about 5%. As the level reaches 15%, a pronounced weakness in the fiber is found. About 10% of the additive is preferred.

EXAMPLE I (Additive)

A sample of the fire retardant additive was prepared as follows:

(1) 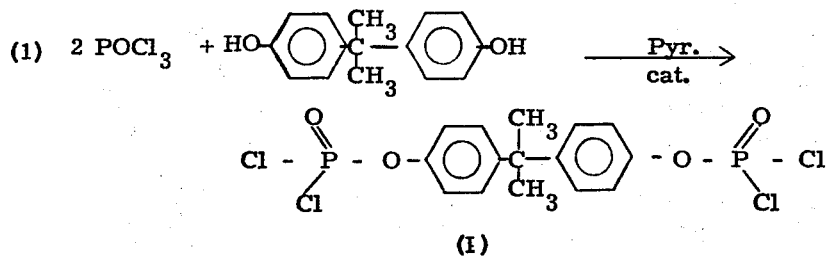

(2) I + 2 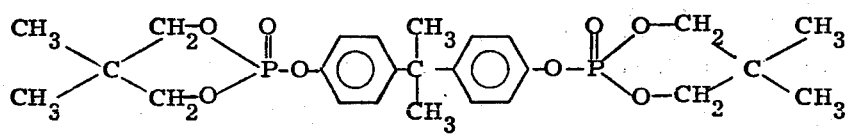

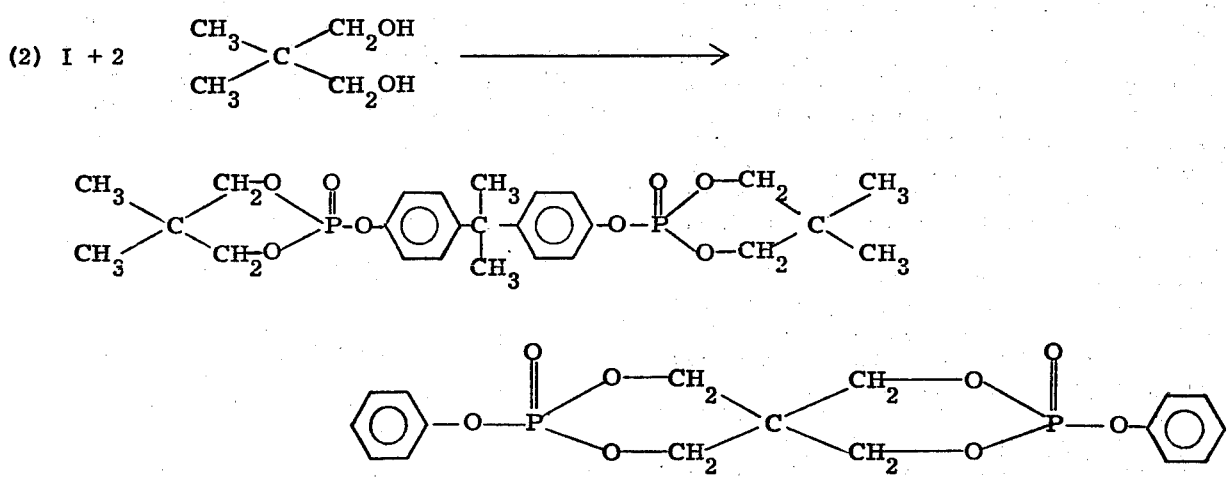

To a flask equipped with a thermometer, cold water, condensor, stirrer and vacuum distillation head was added 228 g (1 mol) of bisphenol A, 353 g. (2.3 mol) $POCl_3$, 3 g. of pyridine and 200 g. toulene. This was heated to reflux over 1¾ hours and held there for 1¼ hours longer. HCl was evolved as an off gas.

Excess $POCl_3$ was distilled off at 80 mm. and 100°C. An additional 100 g. of toulene was added to the reaction pot and the solution then cooled to room temperature. To this was added 208 g. of neopentyl glycol. The reaction was exothermic and HCl gas was evolved. After this addition was completed, the reaction mix was heated to 98°C over 1¼ hours. It was then cooled to room temperature and the resulting crystalline material collected by filtration. The solid was washed with a solution of 15 g. $Na_2CO_3$ in 300 ml. hot water, followed by 600 mls. of benzene and 600 ml. acetone. The crystals were dried to yield product of 75%.

EXAMPLE 2

A sample of a compound of the following structure was prepared as described in U.S. Pat. No. 3,090,799:

EXAMPLE 3

A poly (ethylene terephthalate) prepolymer having a specific viscosity ($N_{sp}$) of 0.043 in phenol/s-tetrachloroethane (60/40) at 0.5 g. $dl^{-1}$ and 25°C was polymerized at 265°C and approximately 1 mm. Hg pressure until the polymer reached a solution specific viscosity greater than 0.28. The polymerization was performed in a 0.5 l stainless steel autoclave. The phosphorus-containing additive was introduced into the molten polymer and mixed with a stirrer for 5 min. The molten polymer was then spun into a 10 filament bundle of fiber. The fiber was drawn over a heated pin at 80°C.

Properties of the fibers were as shown on the following:

Table 1

| Fiber Property | Weight %* 0 | Ex. 2 5.3 | 7.0 | Added to Polymer 9.1 | 11.1 |
|---|---|---|---|---|---|
| Draw Ratio | 4.9 | 3.7 | 4.9 | 4.4 | 3.9 |
| Melting Point (°C) | 256 | 250 | 249 | 247 | 249 |
| Tenacity (g/denier) | 3.4 | 4.0 | 4.3 | 4.0 | 2.4 |
| Ultimate Elongation (%) | 31 | 42 | 10 | 24 | 38 |
| Initial Modulus (g/denier) | 114 | 94 | 138 | 138 | 82 |
| $N_{sp}$ | 0.29 | 0.35 | 0.32 | 0.32 | 0.32 |
| Chemstrand Whiteness ($W_c$) | 82 | 82 | 75 | 85 | 74 |

Table 1-continued

| Fiber Property | Weight %* 0 | Ex. 2 5.3 | 7.0 | Added to Polymer 9.1 | 11.1 |
|---|---|---|---|---|---|

$$*\text{Weight \%} = \frac{\text{Wt. Additive}}{\text{Wt. Additive} + \text{Wt. Polymer}} \times 100$$

Table 2

| Fiber Property | Weight % 0 | Ex. 1 4.8 | 7.0 | Added to Polymer 9.1 | 11.1 |
|---|---|---|---|---|---|
| Draw Ratio | 4.9 | 5.5 | 5.5 | 5.5 | 4.8 |
| Melting Point (°C) | 256 | 251 | 252 | 248 | 247 |
| Tenacity (g/denier) | 3.4 | 5.3 | 5.4 | 4.8 | 3.5 |
| Ultimate Elongation (%) | 31 | 14 | 12 | 12 | 28 |
| Initial Modulus (g/denier) | 114 | 150 | 161 | 137 | 112 |
| $N_{sp}$ | 0.29 | 0.32 | 0.31 | 0.32 | 0.29 |
| Chemstrand Whiteness ($W_c$) | 82 | 85 | 86 | 77 | 72 |

Tristimulus color was measured in a General Electric/Hardy Reflectance Spectrophotometer. Relative brightness is indicated directly by the value of Y. Chromaticity coordinates $x$ and $y$ are calculated from the reflectance measurements, as well known in the art of colorimetry, and more particularly, as described at pages 9–10 of the Massachusetts Institute of Technology *Handbook of Colorimetry* (1936 - The Technology Press, Massachusetts Institute of Technology, Cambridge, Massachusetts.) From the values $x$ and $y$, purity (percent) and dominant wavelength (DWL in nm) is determined from chart 12a in the above cited publication. Chemstrand whiteness ($W_c$) is calculated using the following equation:

$$W_c = 10(Y - 2p^2)^{1/2}$$

where: $Y = Y_{CIE}$ $p$ = purity

Fibers containing either additive were reasonably stable to spinning conditions as shown by the following table in which each additive was added to the polymer at 5 wt. % level and 265°C and then the mixture of additive and polymer is sampled at various times. The rate of specific viscosity change with time was recorded.

Table 3

| Time (min.) | Specific Viscosity None | Example 1 | Example 2 |
|---|---|---|---|
| 0 | 0.343 | 0.285 | 0.335 |
| 5 | 0.339 | 0.240 | 0.326 |
| 15 | 0.338 | 0.238 | 0.324 |
| 30 | 0.330 | 0.228 | 0.321 |
| 45 | 0.342 | 0.224 | 0.311 |
| 60 | 0.324 | 0.223 | 0.290 |
| 75 | 0.335 | 0.219 | 0.305 |

PERMANENCY OF ADDITIVE

The fastness to home-laundering of the phosphorus in the PET filaments was tested by placing knitted tubing of these filaments through typical washing and drying cycles. Portions of the tubing were removed after given numbers of laundering cycles and analyzed for phosphorus content as described under Experimental. One laundering cycle consisted of the following:

1. Approximately 40 g. of tubing was placed in the mini-basket of a General Electric Heavy Duty 16 Washer (Model No. WA 750 EA WH).
2. Approximately 31 ml. of Tide Detergent (Proctor-Gamble) was added for the mini-basket wash.
3. Washer controls were set to permanent press cycle, warm wash, warm rinse, normal wash speed, fast spin speed, mini water level, and no extra rinse.
4. After completion of washing, the tubing was dryed in a General Electric Heavy Duty Versatronic Dryer at high speed setting and permanent press setting.

Tubing was also subjected to simulated commercial dry-cleaning cycles. The dry-cleaning cycle consisted of the following:

1. Approximately 20 g. of tubing was tumbled for 10 min. in 200 ml. of tetrachloroethylene in a bottle containing glass bead.
2. After air drying, the tumbling was repeated in "varsol" solvent.
3. After air drying, the tubing was pressed with a "warm" home iron.

The phosphorus content of fibers containing the fire retardant additives of Examples 1 and 2 before and after laundering are shown in Table 4.

Table 4

| Run No. | Additive | No. Wash & Dry Cycles | Wt. % P | No. Dry Cleaning Cycles | Wt. % P |
|---|---|---|---|---|---|
| 89423 | 7 wt. % of Ex. 2 Additive | 0 | 1.13, 1.01 | 0 | 1.13, 1.01 |
| | | 1 | 1.07, 1.10 | 1 | 1.06, 1.04 |
| | | 5 | 1.18, 1.04 | 4 | 1.11, 1.14 |
| | | 10 | 1.11, 1.05 | | |
| 89420 | 7 wt. % of Ex. 1 Additive | 0 | 0.84, 0.83 | 0 | 0.84, 0.83 |
| | | 1 | 0.88, 0.95 | 1 | 0.86, 0.84 |
| | | 5 | 0.87, 0.84 | 4 | 0.81, 0.85 |
| | | 10 | 0.89, 0.88 | | |
| — | None | 0 | 0.0075, 0.0072 | | |
| | | 1 | 0.0072, 0.0081 | | |

Table 4-continued

| Run No. | Additive | No. Wash & Dry Cycles | Wt. % P | No. Dry Cleaning Cycles | Wt. % P |
|---|---|---|---|---|---|
| | Commercially Available Polyester | 5<br>10 | 0.0073, 0.0067<br>0.0073, 0.0074 | | |

To evaluate the permanence of these additives during dyeing, knit fabrics were dyed with Latyl Brilliant Blue 2G disperse dye using dye baths conditions:
4% dye on wt. of fabric
40:1 liquor:fabric ratio
2 hr. dyeing period.

The carrier dyeing was with 10% Carolid ELF-C (modified biphenyl carrier) on wt. of fabric at 100°C and the pressure dyeing was at 120°C and 15 lb/in². Table 5 shows that 22% of the Example 2 additive and only 11% of Example 1 additive were lost from the fiber under these conditions.

Table 5

| | | Wt. % P in Fiber | |
|---|---|---|---|
| Additive | Undyed | Carrier Dyed | Pressure Dyed |
| Example 1 | 0.8 | 0.7 | 0.7 |
| Example 2 | 0.9 | 0.7 | 0.7 |

EXAMPLE 4

A polyester copolymer formulation in which some polyethylene terephthalate molecules are chain terminated as in Example 23 of U.S. Pat. No. 3,671,495, was spun with 7 wt. % addition of the additives of Example 1 and Example 2. The resulting fibers were dyed at 100°C without carrier with Latyl Brilliant Blue 2G disperse dye. The additives were leached from the fibers during dyeing as illustrated in the following tabulation:

Table 6

| | % P in Fiber | |
|---|---|---|
| | control | dyed |
| Example 2 | 1.1 | 0.6 |
| Example 1 | 0.9 | 0.7 |

Limiting oxygen indices for the additives of Examples 1 and 2 in the fibers described in Example 3 are shown in the Figure.

We claim:

1. The method of imparting fire retardancy to synthetic fibers in which the fiber-forming substance is any long chain synthetic polymer composed of at least 85% by weight of an ester of a dihydric alcohol and terephthalic acid comprising adding to the polymer prior to spinning not more than about 20%, based on the weight of the polymer, of a compound having the general formula:

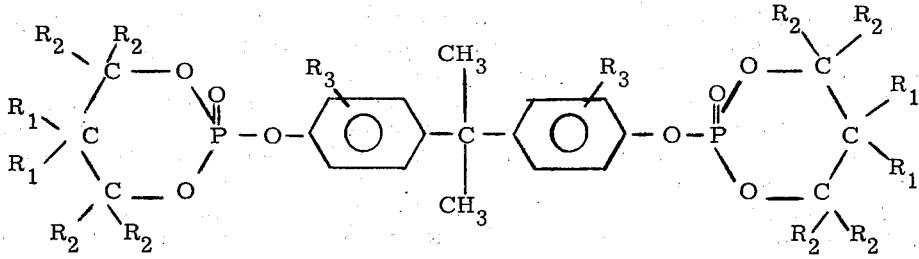

Wherein $R_1$ is an alkyl group containing 1–5 carbon atoms; $R_2$ is a radical selected from the group consisting of H and an alkyl group containing 1–5 carbon atoms; and $R_3$ is a radical selected from the group consisting of hydrogen or a 1–5 carbon alkyl group.

2. The method of claim 1 wherein said compound is added to the polymer in the amount of 5–15%.

3. The method of claim 1 wherein said ester is ethylene terephthalate.

4. The method of claim 1 wherein the compound added is:

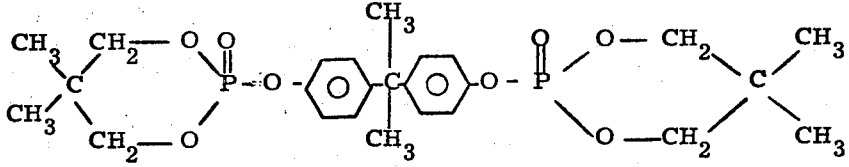

5. The method of claim 4 wherein said compound is added in the amount of about 10%.

6. A synthetic fiber in which the fiber-forming substance is any long chain synthetic polymer comprising at least 85% by weight of an ester of a dihydric alcohol and terephthalic acid and not more than about 20% based on the weight of the polymer, of a compound having the general formula:

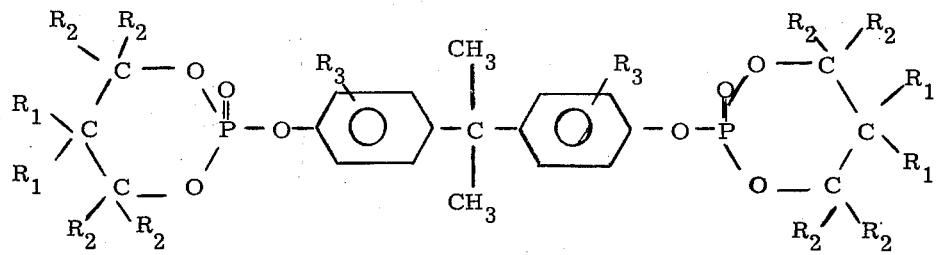

Wherein $R_1$ is an alkyl group containing 1–5 carbon atoms; $R_2$ is a radical selected from the group consisting of H and an alkyl group containing 1–5 carbon atoms; and $R_3$ is a radical selected from the group consisting of hydrogen or a 1–5 carbon alkyl group.

7. The fiber of claim 6 wherein said compound is present in the polymer in the amount of about 5–15%.

8. The fiber of claim 6 wherein the compound is added in the amount of about 10%.

9. The fiber of claim 6 wherein said compound is present in the amount of about 7%.

10. The fiber of claim 9 in which at least about 0.8 weight % of phosphorus is retained in the fiber after five detergent washings.

11. The fiber of claim 6 wherein said ester is ethylene terephthalate.

12. The fiber of claim 6 in which said compound is:

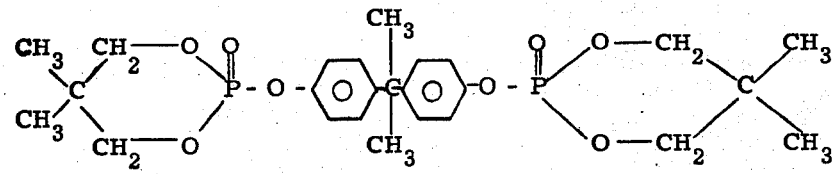

* * * * *